United States Patent [19]

Born et al.

[11] Patent Number: 4,766,228
[45] Date of Patent: Aug. 23, 1988

[54] METAL DIHYDROCARBYL-DITHIOPHOSPHYL-DITHIOPHOSPHATES THEIR MANUFACTURE AND USE AS ADDITIVES FOR LUBRICANTS

[75] Inventors: Maurice Born, Nanterre; Jacques Lallement, Aubervilliers; Pierre Marchand, Orgeval; Guy Parc, Rueil Malmaison; Nicole Thevenin, Paris, all of France

[73] Assignee: Institut Francais du Petrole, Rueil-Malmaison, France

[21] Appl. No.: 904,082

[22] Filed: Sep. 4, 1986

[30] Foreign Application Priority Data

Sep. 4, 1985 [FR] France .................. 85 13236

[51] Int. Cl.$^4$ .............. C07F 3/06; C07F 3/08; C07F 9/90; C07F 9/201
[52] U.S. Cl. .................. 556/25; 556/18; 558/164; 558/165; 252/46.4; 252/32.7 R
[58] Field of Search .............. 556/18, 25; 558/164, 558/165; 252/46.4, 32.7 R

[56] References Cited

U.S. PATENT DOCUMENTS

| | | | |
|---|---|---|---|
| 3,197,404 | 7/1965 | Berger et al. | 556/25 X |
| 3,259,579 | 7/1966 | Rogers et al. | 556/18 X |
| 3,277,133 | 10/1966 | Asseff | 556/25 |
| 3,400,140 | 9/1968 | Rowan et al. | 556/25 |
| 3,402,188 | 9/1968 | Wiese | 556/25 |
| 3,426,054 | 2/1969 | Schneider et al. | 556/25 |
| 3,428,662 | 2/1969 | Millendorf et al. | 556/25 |
| 3,755,501 | 8/1973 | Braid | 558/164 |
| 4,025,458 | 5/1977 | McKay | 556/25 X |
| 4,208,292 | 6/1980 | Bridger | 556/25 X |

*Primary Examiner*—Paul F. Shaver
*Attorney, Agent, or Firm*—Millen & White

[57] ABSTRACT

The invention relates to compounds of the metal dihydrocarbyl-dithiophosphyl-dithiophosphate type, their manufacture and use. These compounds can be represented by the general formula:

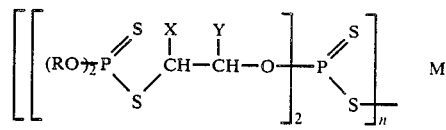

wherein R is a monovalent substantially hydrocarbon-containing radical of 1 to 30 carbon atoms, X and Y are each a hydrogen atom or a monovalent substantially hydrocarbon-containing radical of 1 to 30 carbon atoms, M is a metal selected from zinc, cadmium, lead and antimony or an oxygen- and/or sulfur-containing molybdenum complex, and n is the valence of said metal M. The compounds according to the invention can be used as additives for lubricants wherein they act as a very efficient wear preventive.

11 Claims, No Drawings

METAL DIHYDROCARBYL-DITHIOPHOSPHYL-DITHIOPHOSPHATES THEIR MANUFACTURE AND USE AS ADDITIVES FOR LUBRICANTS

The present invention concerns compounds of the metal dihydrocarbyldithiophosphyl-dithiophosphate type, useful mainly as antioxidants, antiwear, extreme-pressure and anticorrosive additives for lubricating oils. It also concerns a process for manufacturing these compounds and the lubricants containing the same.

BACKGROUND OF THE INVENTION

The metal dialkyl- and diaryl-dithiophosphates, particularly those containing zinc, have been widely used for many years to protect metal surfaces under friction against wear and corrosion, as well as to protect lubricating oils containing the same from oxidation. Details of manufacture of such additives are disclosed for example in U.S. Pat. Nos. 2,364,283—2,364,284,—2,365,93-8,—2,410,650,—2,438,876 and 3,190,833. The metal dialkyl- and dialkylaryl-dithiophosphates disclosed in the prior art are generally characterized by Metal/P/S atomic proportions of 1/2/4—although the sulfur proportion may be higher as the result of a further sulfurization, as described for example in U.S. Pat. No. 2,438,876. An efficient protection against wear requires the use of such products in lubricating oils in proportions by weight generally ranging from 0.5 to 1.5%. On the other hand, German patent No. 948,156 teaches that it is possible to obtain thiolthionophosphoric acid derivatives by reacting a thiolthionophosphoric (or dithiophosphoric) acid diester with ethylene oxide to form a triester of thiolthionophosphoric acid with an oxygenated group, and then treating said product with phosphorus pentasulfide. Although these derivatives are indicated as being liable to form salts with various metals (alkali, alkaline-earth, heavy metals) or with amines, only the preparation of an oleylamine salt is effectively disclosed.

SUMMARY OF THE INVENTION

One object of the invention is to provide new compounds of metal dithiophosphate type, providing particularly protection against wear similar to that achieved with additives of the prior art, but at substantially lower concentrations, or giving better protection at equal concentration. Metal dihydrocarbyl-dithiophosphyl-dithiophosphates according to the invention are complex compounds which can be represented by the general formula (1)

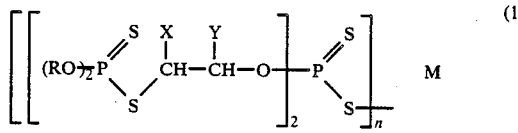

wherein R is a monovalent radical containing substantially hydrocarbons (or a mixture of monovalent radicals containing substantially hydrocarbons) having from 1 to 30 carbon atoms. X and Y each represent a hydrogen atom or a monovalent radical containing substantially hydrocarbons having 1 to 30 carbon atoms, optionally further containing one or more heteroatoms (such for example as oxygen, nitrogen or halogen, etc . . . ); M is a metal selected from zinc, cadmium, lead, antimony or an oxygen- and/or sulfur-containing molybdenum complex group (hereinafter considered as equivalent to metal M), zinc being preferred; n is the valence of the metal M. R radicals may be aliphatic, arylaliphatic, alicyclic, aromatic or alkylaromatic and optionally contain one or more heteroatoms, such as oxygen, nitrogen, sulfur, phosphorus, halogen, etc . . . . The R radical (or a mixture of R radicals) generally originates from monohydroxylated compounds such as monoalcohols or monophenols, substituted or unsubstituted, examples of which will be given hereinafter. The nature of X and Y depends on the epoxide reactant

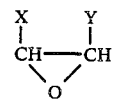

used for the synthesis of the products according to the invention, as hereinafter described.

X and Y may represent, for example, a hydrogen atom or a methyl, chloromethyl or ethyl group; X and Y may also be interconnected and form a poly-methylene chain, for example with four $CH_2$ groups; X and Y may further be longer hydrocarbon chains, for example octyl chains or hydrocarbon chains bearing functional groups such as ester groups, for example alkyl octanoate (more particularly octyl octanoate). When metal M is a divalent metal, the respective atomic proportions of metal, of phosphorus and of sulfur in the compounds of the invention are about 1/6/12.

The metal dithiophosphates according to the invention may be prepared by a process comprising the following steps: A first step (a), wherein a so-called "first generation" dithiophosphoric acid is first prepared, by reaction between a hydroxylated compound (substituted or unsubstituted alcohol or phenol) and phosphorus pentasulfide.

The reaction may be represented by the following equation:

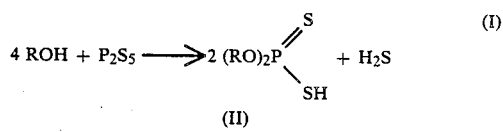

wherein R is defined as precedingly.

Examples of hydroxylated compounds to be used are aliphatic saturated or unsaturated monoalcohols such as methanol, ethanol, propanols, butanols, pentanols, hexanols, heptanols, octanols, nonanols; mixtures of monoalcohols of natural origin (e.g. fusel oil) or of synthetic origin (e.g. alcohols produced by the ALFOL process); alicyclic monoalcohols such as cyclohexanol; halides of aliphatic, alicyclic or aromatic-aliphatic monoalcohols such as, for example, 2-chloro- and 2-bromo-ethanols, chloro- and bromo-propanols, butanols, pentanols, etc . . . ; chloro- or bromo-benzyl alcohols, chloro- or bromo-phenylethyl alcohols.

Further examples are (poly-) alkoxy monoalcohols such for example as (poly-) methoxy-, ethoxy-, propoxy-, butoxy-, phenoxy-, alkylphenoxy-, ethanols and propanols, as well as their halogenated derivatives, and aromatic hydroxylated compounds such as phenol and its substituted derivatives.

It must be understood that, in said step, two or more of the so-defined hydroxylated compounds can be used in admixture. The reaction of the one or more hydroxylated compounds with phosphorus pentasulfide is generally achieved as in the prior art, i.e. at temperatures ranging from 20° to 180° C., preferably from 50° to 150° C., the reactants being used in proportions corresponding to stoichiometric or close thereto. In a second step (b), product (II), obtained in step (a), is reacted with a compound having an epoxide group, such for example as ethylene, propylene, chloropropylene, butylene or cyclohexene oxide or still an oxide of fatty acid ester, particularly an alkyl (e.g. octyl) epoxystearate. Preferably ethylene and propylene oxides are used.

The reaction may be represented by the following equation 2;

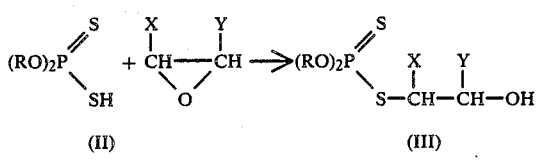

wherein R, X and Y are defined as precedingly.

This is a β-hydroxyalkylation reaction of the compound of formula (II), producing a hydroxylated compound of formula (III) which is a dithiophosphoric alcohol.

This reaction is generally conducted at temperatures ranging from 0° to 150° C., preferably from 20° to 130° C., the reactants being used in proportions corresponding to stoichiometric or close thereto.

In a third step (c), the dithiophosphoric alcohol (III) is reacted with phosphorus pentasulfide, according to a reaction scheme which can be represented by the following equation (3):

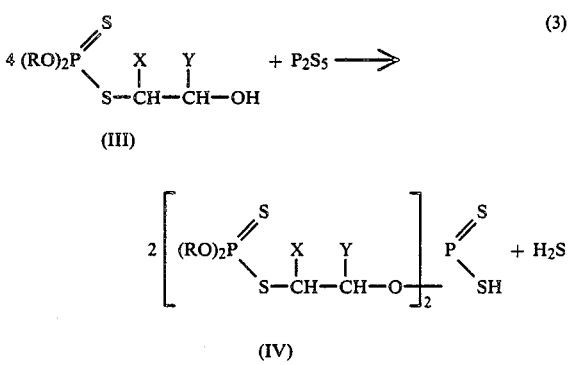

wherein R, X and Y are defined as precedingly. There is obtained a so-called "second generation" dithiophosphyl dithiophosphoric acid (formula IV).

The reaction is perfomed at temperatures generally ranging from 20° to 120° C., preferably from 40° to 90° C., the relative reactants amounts being close to stoichiometric.

In a fourth step (d), the dithiophosphoric acid (IV) is reacted, as alkali metal salt or ammonium salt, with a salt of metal M desired for the final product. The reaction may be represented by the following equation (4):

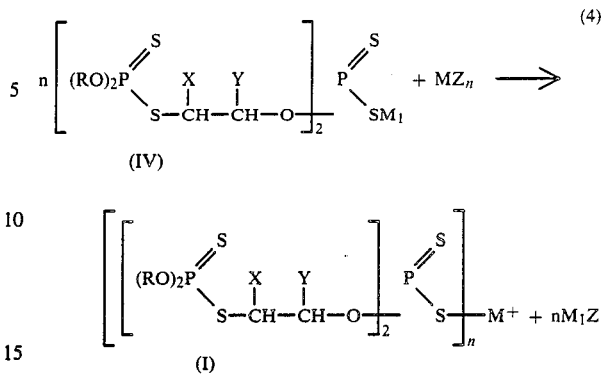

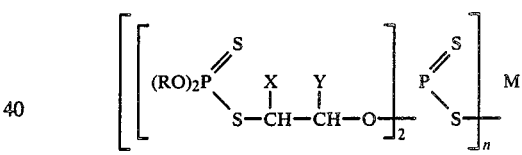

wherein R, S, Y, M and n are defined as precedingly. $M_1$ is an alkali metal or ammonium, Z is one equivalent of the anion of the $MZ_n$ salt. Thus, Z may be a halogen (chlorine or bromine) atom, a nitrate or carboxylate (acetate, formate . . . ) group, or a carbonate, sulfate etc . . . half-group.

The operation is generally conducted in aqueous medium at temperatures ranging from 0° to 100° C., preferably from 40° to 60° C., the $MZ_n$ metal salt being used in excess.

According to a second mode of synthesis of the products of the invention, product (III), obtained in step (b) (dithiophosphoric alcohol), may be directly reacted with phosphorus pentasulfide, in the presence of an oxide or hydroxide of the desired metal M, to give the desired metal dihydrocarbyl-dithiophosphyl-dithiophosphate, complying with the general formula:

metal M optionally being, as precedingly, selected from zinc, cadmium, lead, antimony and molybdenum oxygenated and or sulfurized complex groups. In this reaction, hydrogen sulfide and water are also formed.

The reaction is generally conducted between 40° and 100° C., preferably between 60° and 90° C., in the presence of a solvent used to remove the formed water by azeotropic stripping, the preferred solvent being benzene.

The products of the invention, which may be described as metal dihydrocarbyl-dithiophosphyl-dithiophosphates, may advantageously be used as additives for inorganic and/or synthetic lubricants, particularly for the protection of metal parts against wear and corrosion and for the protection of lubricants against oxidation. These additives may be used at concentrations by weight generally ranging from 0.05 to 2%, but their main advantage is their high anti-wear activity making them satisfactorily efficient at concentrations ranging from 0.05 to 1%.

EXAMPLES

The following examples illustrate the invention but must not be considered in any way as limiting the scope thereof. Example 10 is given by way of comparison.

EXAMPLE 1

In a reactor of 5 liters capacity, provided with a stirrer and purged with nitrogen, 2210 g of 2-butanol (29.8 moles) are introduced. The temperature of the alcohol is brought to about 90° C. by external heating means and then, by means of a feeding device for powdered reactants, 1490 g of $P_2S_5$ (6.7 moles) are introduced in two hours into the stirred alcohol while maintaining the reaction temperature between 90° and 95° C.; then the reaction is continued for two additional hours at a temperature from 95° to 100° C. so as to complete the $P_2S_5$ reaction.

A nitrogen stream is then supplied within the dialkyldithiophosphoric acid (of first generation) for 0.5 hour at 95°-100° C. so as to remove dissolved hydrogen sulfide and the acid is cooled to 25°-30° C. By means of a bromine funnel connected to the reactor, 810 g of propylene oxide (13,95 moles) are introduced into the acid in one hour, while maintaining the reaction temperature between 30° and 35° C.

The reactor is then subjected to a vacuum of 2666 Pa, while simultaneously heating the obtained thiophosphoric alcohol to 100° C.; in these conditions the 2-butanol and propylene oxide excesses are removed by distillation. After cooling, 25 g of filtration earth (diatomaceous) are added and, after filtration, 3375 g of thiophosphoric alcohol are recovered.

In a second reactor of one liter capacity, provided with a stirrer and purged with nitrogen, 240 g of the previously obtained thiophosphoric alcohol (0.8 mole) are introduced and the temperature is increased to 95° C.

By means of a powder feeding device, 37 g (0.166 mole) of $P_2S_5$ are progressively added under stirring in 2 hours, while maintaining the temperature at about 95° C. After cooling and filtration under inert atmosphere in the presence of diatomaceous earth, 209 g of second generation acid (acidity=$1.556 \times 10^{-3}$ acid equivalent/g) are recovered.

This acid is neutralized with a solution of 13 g of sodium hydroxide in 300 cc of water. The obtained milky solution is extracted with three times 500 cc of hexane to remove the excess of thiophosphoric alcohol and a portion of the partly soluble sodium salt, of the acid.

The aqueous solution (lower fraction), containing the purified sodium salt of the acid, is treated for 3 hours under stirring with a solution of 60 g of heptahydrated zinc sulfate $ZnSO_4, 7H_2O$ (0.21 mole) in 150 cc of water.

The obtained milky suspension is extracted with three times 300 cc of benzene, the collected benzene extract is washed with water, dried over anhydrous sodium sulfate, filtered on diatomaceous earth and then evaporated at 100° C. under reduced pressure up to constant weight.

90 g of a translucent very viscous organic product are obtained, whose elementary analysis (Table 1) and RMN 13C, 1H analyses confirm the structure, as well as the infra-red analysis which shows characteristic absorption bands of zinc dialkyldithiophosphates, particularly at 970 $cm^{-1}$ (attributable to P—O—C groups deriving from secondary alcohols), at 665 $cm^{-1}$ (attributable to P=S groups) and at 545 $cm^{-1}$ (attributable to P—S groups) and at 545 $cm^{-1}$ (attributable to P—S groups) these absorption bands appear to be substantially more intense than those of the corresponding conventional zinc di-sec-butyl dithiophosphate, particularly for P=S and P—S bands.

The product obtained complies with the formula:

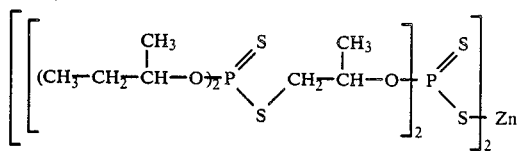

EXAMPLE 2

The experiment of example 1 is repeated by reacting the aqueous solution of the purified sodium salt of "second generation" dithiophosphoric acid prepared from 240 g of thiophosphoric alcohol, with 79.6 g of trihydrated lead acetate $Pb(OOCH_3)_2,3H_2O$ dissolved in 150 cc of water. After treatment, about 100 g of organic product are recovered whose elemental analysis (Table 1), RMN 13C, 1H and infra-red analyses confirm the structure complying with the formula:

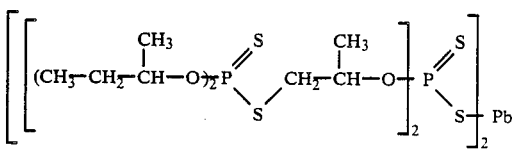

EXAMPLE 3

The experiment of example 2 is repeated by reacting 56 g of dihydrated cadmium acetate $Cd(OOCCH_3)_2, 2H_2O$ (0.21 mole); 80 g of product are recovered whose elemental analysis (Table 1), RMN 13C, 1H and infra-red analyses confirm the structure, complying with the formula:

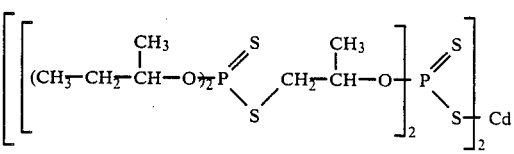

TABLE 1

$$\left[\left[(CH_3-CH_2-CH(CH_3)-O)_2 P\underset{S}{\overset{S}{\diagup\!\!\!\diagdown}} CH_2-CH(CH_3)-O\right]_2 P\underset{S-}{\overset{S}{\diagup\!\!\!\diagdown}}\right]_2 M$$

| PRODUCT OF EXAMPLE | METAL M | % WEIGHT THEORY | | | | | % WEIGHT FOUND | | | | | METAL/P/S IN ATOMS | |
|---|---|---|---|---|---|---|---|---|---|---|---|---|---|
| | | C | H | S | P | METAL | C | H | S* | P** | METAL*** | theory | found |
| 1 | Zn | 36.36 | 6.66 | 26.48 | 12.79 | 4.50 | 36.65 | 6.59 | 27.02 | 12.40 | 4.47 | | 1/5.85/12.32 |
| 2 | Pb | 33.13 | 6.07 | 24.12 | 11.65 | 12.99 | 33.8 | 6.24 | 23.84 | 11.20 | 12.40 | 1/6/12 | 1/6.04/12.42 |
| 3 | Cd | 35.22 | 6.45 | 25.65 | 12.30 | 7.49 | 35.84 | 6.65 | 25.34 | 12.20 | 7.20 | | 1/6.15/12.34 |

*determination by LECO methode
**determination by X fluorescence
***determination by EDTA complexometry

EXAMPLE 4

In a reactor of one liter capacity, equipped with a stirrer, a DEAN-STARK separator with cooler and a feeding system for powdered reactants, 200 g (0.66 mole) of the thiophosphoric alcohol prepared in example 1, 300 cc of benzene and 20.3 g (0.25 mole) of ZnO, are introduced under an inert atmosphere.

The obtained suspension is heated under stirring up to benzene reflux; the temperature of the medium ranges from 85° to 90° C.

By means of the system for feeding powdered reactants, 36.7 g (0.165 mole) of P$_2$S$_5$ are progressively added in 3 hours. Resultant "second generation" acid reacts with ZnO; the water produced by the reaction is removed, as it is formed, by azeotropic stripping in a DEAN-STARK separator. The mixture is maintained for 3 additional hours at reflux and then allowed to cool.

The benzene solution is then filtered, in the presence of diatomaceous earth, then evaporated at 100° C. under reduced pressure up to constant weight.

225 g of a viscous product are thus recovered, whose elemental analysis (Table II), RMN 13C, 1H and infrared analyses confirm the structure, corresponding to the formula:

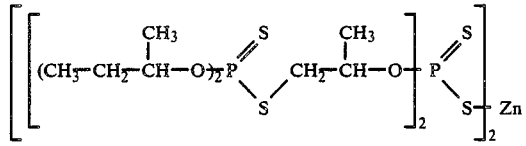

EXAMPLE 5

The experiment of example 4 is repeated with the use of 224.4 g (2.2 moles) OF 4-methyl 2-pentanol and of 11.1 g (0.5 mole) of P$_2$S$_5$; the temperature of formation of the "first generation" acid is 85°–90° C.

After removal of the dissolved H$_2$S, by bubbling of a nitrogen stream, the acid is converted to thiophosphoric alcohol by addition, at 30°–35° C., of 60.9 g (1.05 mole) of propylene oxide. The alcohol and propylene oxide excesses are removed by heating at 100° C. under reduced pressure.

Then 400 cc of benzene and 25 g (0.31 mole) of ZnO are added and the mixture is brought to reflux (87°–90° C.) under stirring. Then, 53.3 g (0.24 mole) of P$_2$S$_5$ are progressively added in 3 hours; the water produced in the reaction being progressively carried away by the heteroazeotropic effect of the solvent.

After 3 further hours of reflux, filtration and evaporation 367 g of a viscous translucent product are obtained whose elemental analysis (Table II), RMN 13C, 1H and infra-red analyses confirm the structure, corresponding to the formula:

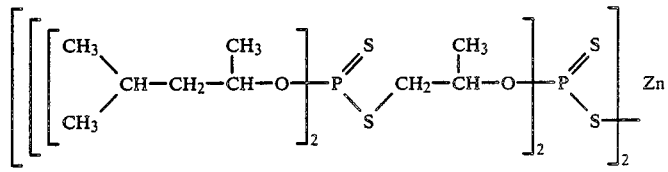

EXAMPLE 6

The experiment of example 4 is repeated with the use of 286 g (2.2 moles) of 2-octanol, 111.1 g (0.5 mole) of P$_2$S$_5$ and 60.9 g (1.05 mole) of propylene oxide. The temperature at which the "first generation" acid forms is between 115° and 120° C.

After removal of the excess reactants and of dissolved H$_2$S, the mixture is allowed to cool and then 400 cc of benzene and 25 g (0.31 mole) of ZnO are added and the mixture is brought to reflux. Then 52.7 g (0.237 mole) of P$_2$S$_5$ are added in 3 hours, and the reaction is continued for 4 additional hours, the reaction water being removed continuously.

After cooling, filtration on diatomaceous earth and evaporation under reduced pressure, 432 g of a translucent viscous product are recovered whose elemental analysis (table II), RMN 13C, 1H and infra-red analyses confirm the structure, corresponding to the formula:

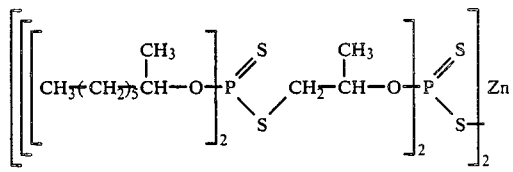

EXAMPLE 7

The experiment of example 5 is repeated with the use of 262.44 g (1 mole) of dodecylphenol and 52.78 g (0.2375 mole) of $P_2S_5$; the temperature of formation of the "first generation" dithiophosphoric acid is 145°-155° C.

After removal of the dissolved $H_2S$, by nitrogen bubbling, the acid is converted to thiophosphoric alcohol by addition, at 30°-35° C., of 28.93 g (0.5 mole) of propylene oxide. The excess of propylene oxide is removed by heating at 100° C. under reduced pressure.

Then 400 cc of benzene and 38.7 g of ZnO (0.475 mole) are added to the mixture which is then brought to reflux.

Then 7.23 g of $P_2S_5$ (0.119 mole) are progressively introduced in 3 hours; the water produced in the reaction is continuously removed by heteroazeotropic stripping.

After 3 additional hours of reflux, filtration through diatomaceous earth and evaporation under reduced pressure, 332 g of product are recovered whose elemental analysis (Table II), RMN 13C, 1H and infra-red analyses, confirm the structure, corresponding to the formula:

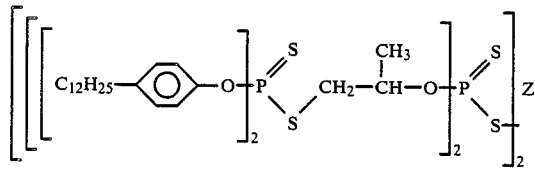

EXAMPLE 8

The experiment of example 4 is repeated with the use of a mixture of 81.4 g (1.1 mole) of n-butanol, 143 g (1.1 mole) of 2-octanol, 111.1 g (0.5 mole) of $P_2S_5$, 60.9 g (1.05 mole) of propylene oxide and 25 g (0.31 mole) of ZnO; the temperature of formation of the "first generation" acid is 115° C. The preparation of the desired product is continued in the conditions of example 6.

325 g of translucent, viscous product are recovered, whose elemental analysis (Table II), RMN 13C, 1H and infra-red analyses confirm the structure, corresponding to the formula:

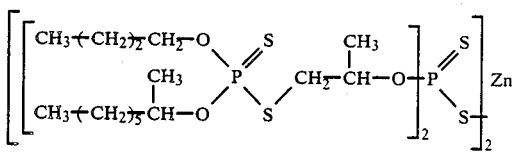

this formula being an overall formula representative of a mixture of products containing similar proportions of groups derived from n-butanol and from 2-octanol.

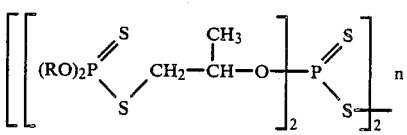

| Product of Example | RO— | % WEIGHT Theory | | | | | % WEIGHT Found | | | | | Zn/P/S in atoms | |
|---|---|---|---|---|---|---|---|---|---|---|---|---|---|
| | | C | H | S | P | Zn | C | H | S | P | Zn | Theory | Found |
| 4 | $CH_3-CH_2-\underset{\underset{CH_3}{|}}{CH}-O-$ | 36.36 | 6.66 | 26.48 | 12.79 | 4.50 | 36.71 | 6.92 | 26.8 | 12.20 | 4.30 | 1/6/12 | 1/6/12.7 |
| 5 | $CH_3-\underset{\underset{CH_3}{|}}{CH}-CH_2-\underset{\underset{CH_3}{|}}{CH}-O-$ | 42.96 | 7.69 | 22.94 | 11.08 | 3.90 | 43.15 | 8.10 | 23.5 | 10.74 | 3.76 | 1/6/12 | 1/5.82/12.7 |
| 6 | $CH_3\text{-}(CH_2)_5\text{-}\underset{\underset{CH_3}{|}}{CH}-O-$ | 47.99 | 8.48 | 20.23 | 9.77 | 3.44 | 48.50 | 8.62 | 19.62 | 9.40 | 3.20 | 1/6/12 | 1/6.2/12.5 |
| 7 | $C_{12}H_{25}-\bigcirc-O-$ | 63.31 | 8.72 | 13.00 | 6.28 | 2.21 | 64.1 | 8.70 | 12.30 | 6.10 | 2.17 | 1/6/12 | 1/5.93/11.5 |
| 8 | $CH_3\text{-}(CH_2)_2\text{-}CH_2-O-$ (50%) $CH_3\text{-}(CH_2)_5\text{-}\underset{\underset{CH_3}{|}}{CH}-O-$ (50%) | 42.96 | 7.69 | 22.94 | 11.08 | 3.90 | 43.27 | 7.98 | 23.3 | 10.89 | 3.82 | 1/6/12 | 1/6.02/12.43 |

EXAMPLE 9

The experiment of example 7 is repeated, except that propylene oxide is replaced with the same molar amount of ethylene oxide. At the end of the experiment, 314 g of product are recovered, whose elemental analysis is as follows:

| ELEMENT | % WEIGHT THEORY | FOUND |
|---|---|---|
| C | 62.88 | 64.31 |
| H | 8.61 | 8.70 |
| S | 13.25 | 13.4 |
| P | 6.40 | 6.1 |
| Zn | 2.25 | 2.28 |
| Zn/P/S | 1/6/12 | 1/5.64/12 |

| | % WEIGHT | |
|---|---|---|
| ELEMENT | THEORY | FOUND |
| in atoms | | |

The RMN 13C, 1H and infra-red analyses confirm the structure corresponding to the formula:

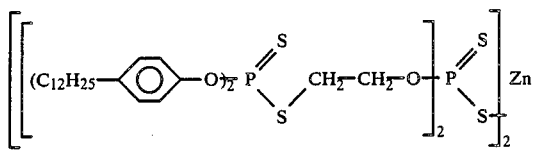

EXAMPLE 10

(comparative)

An amine salt corresponding to the teaching of German patent 948,156 has also been prepared as follows:

In a reactor of 0.5 liter, 100 g of a so-called "second generation" acid are prepared (acidity = $1.556 \times 10^{-3}$ acid eq./g) according to the method described in example 1.

41.6 g of oleylamine, i.e. the stoichiometric amount required for neutralizing the acid, are added. After exothermic reaction, the mixture is heated for 3 hours to complete the reaction.

After filtration, 127 g of product are recovered whose elemental analysis indicates the following P, S and N contents.

| | Found | Theory |
|---|---|---|
| P % weight | 9.25 | 9.66 |
| S % weight | 20.52 | 20.00 |
| N % weight | 1.45 | 1.46 |

This confirms the structure of the oleylamine salt, which may be represented by the formula:

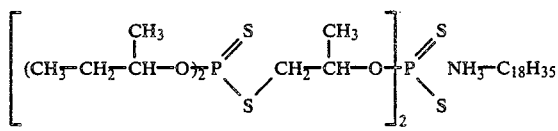

EXAMPLE 11

Tests

The anti-wear properties of the additives prepared according to the preceding examples have geen evidenced by means of an XL 5 PEUGEOT engine with overhead camshaft.

The arrangement used for the tests consists of two cylinder heads of an XL 5 PEUGEOT engine mounted on supports adapted for an oil circulation through the system. The camshafts are driven directly at their end by two-speed electric motors. An oil pump system is provided to reconstruct the normal conditions of a complete engine, as well as the pressurization of the circuit before actuation of the camshafts.

A fine filtration (substantially 10 μm) provides for the removal of most of the particles formed by friction.

The main test conditions are as follows:
running speed:
 1 minute at 750 r.p.m.
 2 minutes at 1500 r.p.m.
operating time: 50 hours
oil temperature: 50° C.
feeding pressure of the valve rockers: 2 bars at 50° C.
charge of the springs at maximum lifting: 1200N
intermediary clearance adjustment at 25 hours
application of pressure and temperature to camshafts
 before starting the driving engines.

The anti-wear properties of the additives are evaluated by averaging the wear of the valve rockers after test (average wear of the 16 valve rockers).

The lubricating oil consists of a 175 Neutral solvent mineral oil, containing:
3.35% by weight of detergent additive (Ca = 1800 ppm)
5% by weight of ashless dispersing additive.

Three series of experiments have been conducted, one with the use of zinc dithiophosphate of example 1 (Zn/P/S = 1/5.85/12.32), a second one by means of the oleylamine salt of example 10 and a third one by means of the conventional zinc dithiophosphate obtained from 2-butanol (Zn/P/S = 1/2/4/); the results are summarized in Table III hereinafter:

TABLE III

| | ADDITIVE | | | |
|---|---|---|---|---|
| NATURE | Additive in oil (weight %) | Zn in oil (ppm) | P in oil (ppm) | * Average wear of valve rockers mg/valve rocker |
| NONE | 0 | 0 | 0 | ** |
| [(CH₃—CH₂—CH(CH₃)—O)₂P(=S)S]₂Zn conventional | 1.174 | 1400 | 1326 | 14.7 |
| | 0.782 | 933 | 884 | 15.6 |
| | 0.391 | 466 | 442 | 17.0 |
| | 0.293 | 350 | 331 | 26.2 |

TABLE III-continued

| NATURE | Additive in oil (weight %) | Zn in oil (ppm) | P in oil (ppm) | Average wear of valve rockers mg/valve rocker* |
|---|---|---|---|---|
| 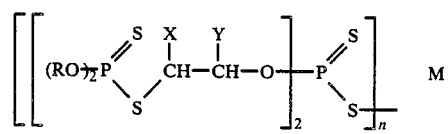 of example 10 | 1.433 | 0 | 1326 | 23.7 |
|  | 0.956 | 0 | 884 | 28.0 |
| 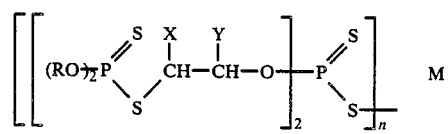 of example 1 | 1.069 | 478 | 1326 | 12.9 |
|  | 0.713 | 319 | 884 | 13.5 |
|  | 0.260 | 116 | 322 | 13.2 |
|  | 0.130 | 58 | 161 | 14.1 |

*average wear calculated on 16 valve rockers (8 by cylinderhead)
**destruction of the valve rockers after a few hours of test Table III shows a high anti-wear activity for one of the additives according to the invention as compared with the conventional zinc dithiophosphate obtained from the same initial alcohol and with the reaction product between oleylamine and "second generation" dithiophosphoric acid.

As a matter of fact, it is observed that, for commercial dithiophosphate and for amine dithiophosphate, the protection of the valve rockers against wear continuously decreases with a decrease of the lubricant phosphorus content, particularly below about 1500 ppm of phosphorus, whereas on the contrary, with one of the products of the invention, this protection is achieved even at phosphorus contents as low as about 160 ppm.

The same experiments, performed with identical molar amounts of additives of examples 2 to 9 give similar results.

What is claimed as the invention is:

1. A compound of metal dihydrocarbyl-dithiophosphyl-dithiophosphate type, represented by the general formula:

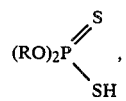

wherein R is at least one monovalent substantially hydrocarbon-containing radical of 1 to 30 carbon atoms; X and Y are each a hydrogen atom or a substantially hydrocarbon-containing radical of 1 to 30 carbon atoms and may be optionally interconnected to form a polymethylene chain, M is a metal selected from zinc, cadmium lead and antimony; and n is the valence of the metal.

2. A compound according to claim 1, wherein R is at least one aliphatic, arylaliphatic, alicyclic, aromatic or alkyl-aromatic radical, derived from an aliphatic or alicyclic monoalcohols or from a monophenol or a monophenol substituted by at least one alkyl group.

3. A Compound according to claim 1, wherein X and Y are each hydrogen, methyl, chloromethyl, ethyl, octyl or alkyl octanoate, or together form a polymethylene chain with four CH$_2$ groups.

4. A compound according to claim 1, wherein N is zinc.

5. A compound according to claim 1, wherein metal M is in a divalent state and the respective atomic proportions of said metal M, of phosphorus and of sulfur in said compound are about 1/6/12.

6. A process for manufacturing a compound according to claim 1, comprising:

(a) reacting a hydroxylated compound ROH with phosphorus pentasulfide to form a dithiophosphoric acid of the formula:

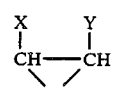

R being defined as in claim 1;

(b) reacting the dithiophosphoric acid obtained in step (a) with a compound having an epoxide group

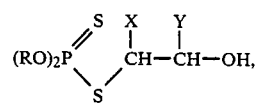

to form a dithiophosphoric alcohol of the formula

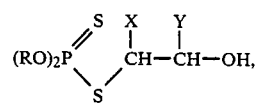

X and Y being defined as in claim 1;

(c) reacting the dithiophosphoric alcohol obtained in step (b) with phosphorus pentasulfide to form a dithiophosphyl-dithiophosphoric acid of the formula:

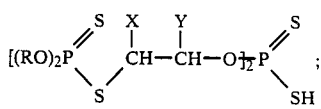

and
(d) reacting the dithiophosphyl-dithiophosphoric acid obtained in step (c) with a basic compound to obtain the alkali metal or ammonium salt, and
(e) reacting the salt obtained in step (d) with a salt of metal M, to form the desired compound of the formula:

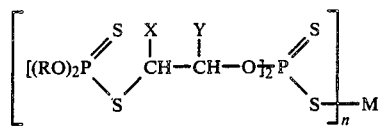

7. A process for manufacturing a compound according to 1, characterized by the steps of:
(a) reacting a hydroxylated compound ROH with phosphorus pentasulfide to form a dithiophosphoric acid complying with the formula:

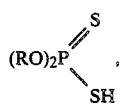

R being defined as in claim 1;
(b) reacting the dithiophosphoric acid obtained in step (a) with a compound having an epoxide group

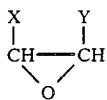

to form a dithiophosphoric alcohol of the formula:

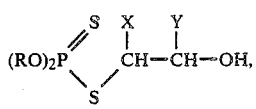

X and Y being defined as in claim 1; and
(c) reacting the dithiophosphoric alcohol obtained in step (b) with phosphorus pentasulfide in the presence of an oxide or hydroxide of said metal M, to form the desired compound.

8. A process according to claim 7, characterized in that step (c) is performed in the presence of a solvent adapted to remove the formed water by azeotropic stripping.

9. A lubricating composition, comprising a major proportion of mineral or synthetic lubricating oil and a minor proportion from 0.05 to 2% by weight of at least one compound according to claim 1.

10. A composition according to claim 9, characterized in that said minor proportion is from 0.05 to 1% by weight.

11. A compound according to claim 2, wherein the aliphatic, acylaliphatic, alicyclic, aromatic or alkylaromatic radical contains at least one hetero atom.

* * * * *